US012521100B2

(12) United States Patent
Chen

(10) Patent No.: US 12,521,100 B2
(45) Date of Patent: Jan. 13, 2026

(54) MULTI-LAYER NESTED INNER CONTAINER EASY TO DISASSEMBLE AND CLEAN AND SPERM EXTRACTOR COMPRISING SAME

(71) Applicant: UC GLOBAL TRADE INC, Chino, CA (US)

(72) Inventor: Junjun Chen, Shenzhen (CN)

(73) Assignee: UC GLOBAL TRADE INC, Chino, CA (US)

( * ) Notice: Subject to any disclaimer, the term of this patent is extended or adjusted under 35 U.S.C. 154(b) by 582 days.

(21) Appl. No.: 18/067,717

(22) Filed: Dec. 18, 2022

(65) Prior Publication Data

US 2023/0371932 A1 Nov. 23, 2023

(30) Foreign Application Priority Data

May 18, 2022 (CN) ......................... 202221192060.4

(51) Int. Cl.

| | |
|---|---|
| ***A61B 10/00*** | (2006.01) |
| ***A61H 19/00*** | (2006.01) |
| ***B65D 1/02*** | (2006.01) |
| ***B65D 8/00*** | (2006.01) |
| ***B65D 77/04*** | (2006.01) |

(52) U.S. Cl.

CPC ........ *A61B 10/0058* (2013.01); *B65D 1/0215* (2013.01); *B65D 15/16* (2013.01); *B65D 77/04* (2013.01); *A61H 19/50* (2013.01)

(58) Field of Classification Search

CPC ...... A61F 5/451; A61F 5/453; A61B 10/0058; B65D 1/0215; B65D 15/16; B65D 77/04; A61H 19/50

See application file for complete search history.

(56) References Cited

U.S. PATENT DOCUMENTS

| | | | | |
|---|---|---|---|---|
| 11,752,063 B1 * | 9/2023 | Huang | .................. | A61H 19/32 600/38 |
| 12,146,488 B2 * | 11/2024 | Spybey | ..................... | F04B 9/14 |
| 2004/0166263 A1 * | 8/2004 | Nahill | ................. | B65D 1/0215 428/35.7 |
| 2008/0004577 A1 * | 1/2008 | Matsuura | ............. | A61F 5/0096 604/317 |

(Continued)

FOREIGN PATENT DOCUMENTS

CN 109106401 B * 7/2021 ............. A61H 7/004

*Primary Examiner* — Susan S Su

(74) *Attorney, Agent, or Firm* — HOWARD M COHN and Associates, LLC

(57) ABSTRACT

The utility model discloses a multi-layer nested inner container easy to disassemble and clean and a sperm extractor comprising the same. A soft cup is arranged in a cavity of a hard inner long cylinder in an interference fit manner to form a detachable assembly; the soft cup can be well fixed by means of the hard inner long cylinder, and the soft material of the soft cup makes the interference fit structure easy to assemble and stable; and an outer surface of the hard inner long cylinder is provided with stoppers, and the stoppers abut against an outer cylinder to form interference fit. In this way, when the soft cup is pulled out, the hard inner long cylinder can be used as an acting point, which facilitates assembly and cleaning. In addition, the snap fit assembly mode is simple, so assembly efficiency is improved.

6 Claims, 2 Drawing Sheets

(56) References Cited

U.S. PATENT DOCUMENTS

| | | | | |
|---|---|---|---|---|
| 2013/0253458 | A1* | 9/2013 | Wu | A61H 19/32 604/349 |
| 2018/0021212 | A1* | 1/2018 | Matsuura | A61H 9/0057 600/38 |
| 2021/0186798 | A1* | 6/2021 | Tang | A61H 19/32 |
| 2021/0212669 | A1* | 7/2021 | Pratt | A61B 5/150351 |
| 2021/0401410 | A1* | 12/2021 | Prien | A61B 10/0058 |

* cited by examiner

MULTI-LAYER NESTED INNER CONTAINER EASY TO DISASSEMBLE AND CLEAN AND SPERM EXTRACTOR COMPRISING SAME

BACKGROUND OF THE INVENTION

1. Technical Field

The utility model relates to the technical field of medical instruments, in particular to a multi-layer nested sperm extractor easy to disassemble and clean.

2. Description of Related Art

A sperm extractor is a medical instrument used to assist sperm collection, and generally comprises a main housing, a soft cup and a driving component controlling the movement of the soft cup. The driving component controls the soft cup to expand and contract, rotate and vibrate, to generate a stimulation effect, thus improving sperm extraction efficiency. Cleaning and maintenance of the sperm extractor are very important, so the disassembly of the soft cup should be easy. In addition, the soft cups of some sperm extractors may hit the internal structure occasionally when expanding, which affects use experience.

Current soft cups are mainly made of soft TPE/TPR/silicone, so that an inner wall of the soft cup has good elasticity and wrapping property, and the soft cups are generally washable for repeated use. In the prior art, some sperm extractors only comprise a soft cup, which cannot realize electric functions, and are generally too soft to be easily held in place and air-dried; and some sperm extractors comprise an inner container component formed by wrapping a soft cup with a hard plastic shell, the inner container component is then fixed to an outer housing, and such structure is often fixed by using a fixing pin or fastening, which is very inconvenient to disassemble. Therefore, there is an urgent need for a sperm extractor easy to clean and disassemble.

BRIEF SUMMARY OF THE INVENTION

Aiming at the problem that the structural design of existing sperm extractors does not facilitate cleaning and disassembly in the prior art, a technical scheme is provided.

Further, the problem that when a soft cup is fit into a hard plastic shell, a gap may be generated due to excessive resistance also needs to be solved in the optimized scheme.

To achieve the above purpose, the utility model provides a multi-layer nested inner container easy to disassemble and clean, which comprises a soft cup, a hard inner long cylinder and an outer cylinder, wherein the soft cup is arranged in a cavity of the hard inner long cylinder in an interference fit manner to form a detachable assembly, the hard inner long cylinder is sleeved with the outer cylinder with a gap between the two, at least part of an outer surface of the hard inner long cylinder is provided with stoppers, and the stoppers abut against the outer cylinder to form interference fit.

Preferably, a side wall of the hard inner long cylinder is further provided with a plurality of through holes at intervals, and the stoppers are embedded in the side wall between adjacent through holes.

Preferably, the stoppers are silicone strips, and the silicone strip partially protrudes from a surface of the hard inner long cylinder.

Preferably, a surface of the stopper facing the outer cylinder is a friction surface.

Preferably, the hard inner long cylinder and the outer cylinder are made of hard plastic.

A sperm extractor is further provided, which comprises the multi-layer nested inner container as described above, and further comprises an outer housing and a control component, wherein the inner container is fixed in an inner cavity of the outer housing in a snap fit manner, an opening of the outer housing is in the same direction as an opening of the inner container, the inner cavity of the outer housing also contains the control component, and a vibration part of the control component is connected with the soft cup to control the vibration of the soft cup.

Preferably, the opening of the outer housing is further provided with a guide ring in a snap fit manner, and a protective cover is arranged on the guide ring.

Preferably, the control component comprises a battery, a circuit board and a vibration motor which are electrically connected, the circuit board and the battery are fixed to the outer housing, and an output end of the vibration motor is connected with a bottom of the soft cup.

The utility model has the following beneficial effects. The utility model discloses a multi-layer nested inner container easy to disassemble and clean and a sperm extractor comprising the same. The inner container comprises a soft cup, a hard inner long cylinder and an outer cylinder; the soft cup is arranged in a cavity of the hard inner long cylinder in an interference fit manner to form a detachable assembly; the soft cup can be well fixed by means of the hard inner long cylinder, and the soft material of the soft cup makes the interference fit structure easy to assemble and stable; the hard inner long cylinder is sleeved with the outer cylinder with a gap between the two; and at least part of an outer surface of the hard inner long cylinder is provided with stoppers, and the stoppers abut against the outer cylinder to form interference fit. Through the stoppers, snap fit is realized, so when the soft cup is pulled out, the hard inner long cylinder can be used as an acting point, which facilitates assembly and cleaning. In addition, the snap fit assembly mode is simple, so assembly efficiency is improved. Further, in the optimized scheme, the hard inner long cylinder is provided with through holes, and a user can reach to and hold the soft cup through the through holes for assembly, so that the assembly process is simple and the structure is more stable.

BRIEF DESCRIPTION OF THE SEVERAL VIEWS OF THE DRAWINGS

Main elements and corresponding symbols.

1. soft cup;
2. hard inner long cylinder; 21. through hole;
3. outer cylinder;
4. stopper;
5. outer housing; 51. guide ring; 52. protective cover;

6. control component; 61. battery; 62. circuit board; 63. vibration motor.

DETAILED DESCRIPTION OF THE INVENTION

In order to express the utility model more clearly, the utility model will be further described below in conjunction with attached drawings.

In the following description, details of generally selected examples are given to provide a deeper understanding of the utility model. Obviously, the described embodiments are only part of the embodiments of the utility model, but not all of them. It should be understood that the specific embodiments are only used to explain the utility model, but not to limit the utility model.

It should be understood that when the terms "include" and/or "comprise" are used in this specification, they specify the presence of stated features, integers, steps, operations, elements or components, but do not exclude the presence or addition of one or more other features, integers, steps, operations, elements, components or their combinations.

Figure 1:
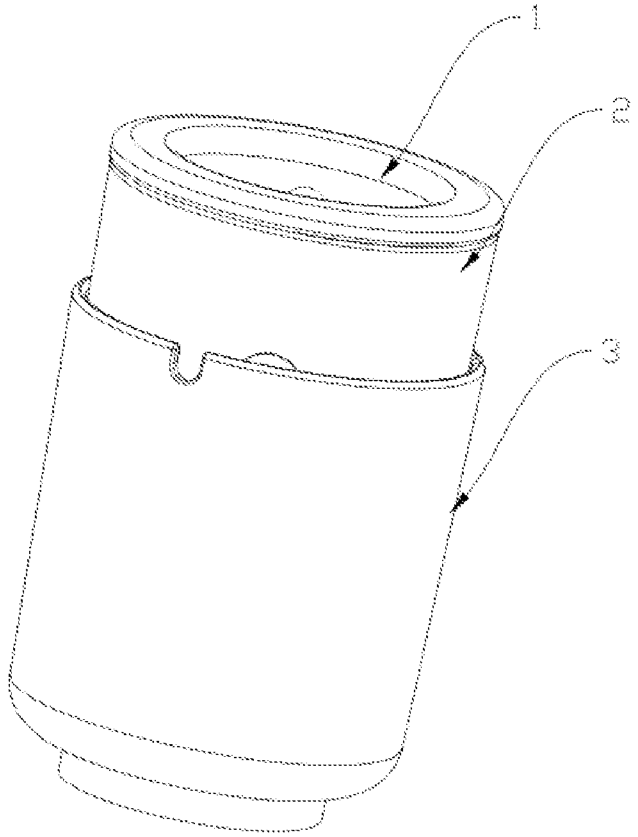
FIG. 1 is a perspective view of an inner container of the utility model.
Figure 2:
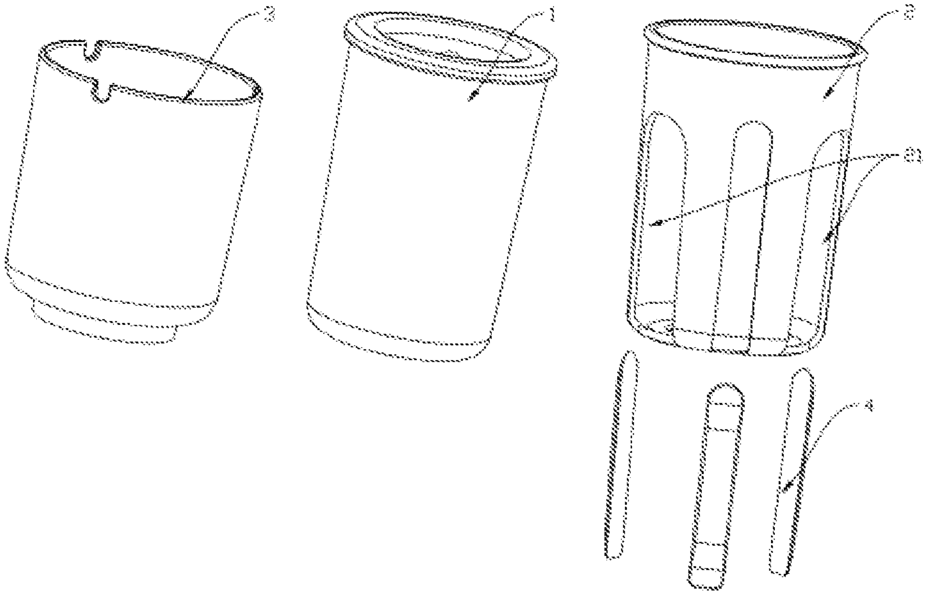
FIG. 2 is an explosive view of an inner container of the utility model.

The utility model discloses a multi-layer nested inner container easy to disassemble and clean. Refer to FIGS. 1-2, the inner container comprises a soft cup 1, a hard inner long cylinder 2 and an outer cylinder 3; the soft cup 1 is arranged in a cavity of the hard inner long cylinder 2 in an interference fit manner to form a detachable assembly; the soft cup can be well fixed by means of the hard inner long cylinder, and the soft material of the soft cup makes the interference fit structure easy to assemble and stable; the hard inner long cylinder is sleeved with the outer cylinder with a gap between the two; and at least part of an outer surface of the hard inner long cylinder 2 is provided with stoppers 4 which fill the gap between the hard inner cylinder and the outer cylinder, and due to the fact that the stoppers only generate snap-fit and stopping effects locally, the relative contact area is small, so while fixing is realized, the force required for pulling out during disassembly does not have to be very large. The stopper 4 abuts against the outer cylinder to form interference fit, so the stopper can be made of hard materials or malleable materials.

In this embodiment, a plurality of through holes 21 are formed at intervals on a side wall of the hard inner long cylinder 2, and the stoppers are embedded in the side wall between adjacent through holes. Because the soft cup is made of TPE/TPR/silicone, friction resistance tends to be generated when the soft cup is fit into the hard inner long cylinder, and a sealing structure may be formed so that part of the gas cannot be discharged from the cavity of the hard inner long cylinder, so assembly is very inconvenient. By arranging the through holes in this scheme, the gas can be discharged conveniently, and a user can reach to and hold the soft cup through the through holes to fit the soft cup into the hard inner long cylinder more easily, so that the soft cup can be better attached to an inner surface of the hard inner long cylinder.

In this embodiment, the stopper 4 is a silicone strip, and the silicone strip partially protrudes from a surface of the hard inner long cylinder. The silicone strip has certain ductility, so as to provide good friction, thus enhancing structural stability.

In this embodiment, a surface of the stopper facing the outer cylinder is a friction surface.

In this embodiment, the hard inner long cylinder and the outer cylinder are made of hard plastic.

Figure 3:
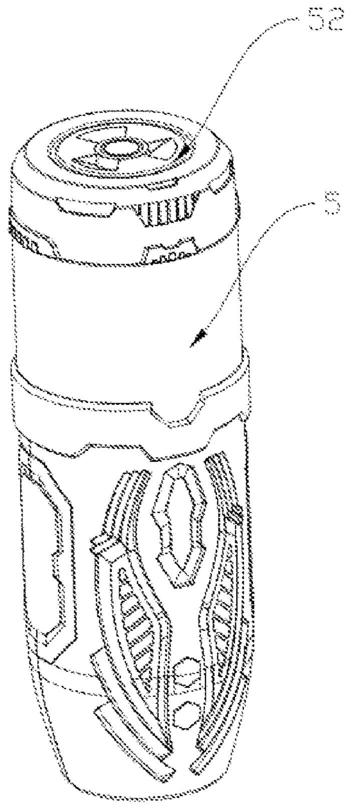
FIG. 3 is a perspective view of a sperm extractor of the utility model.
Figure 4:
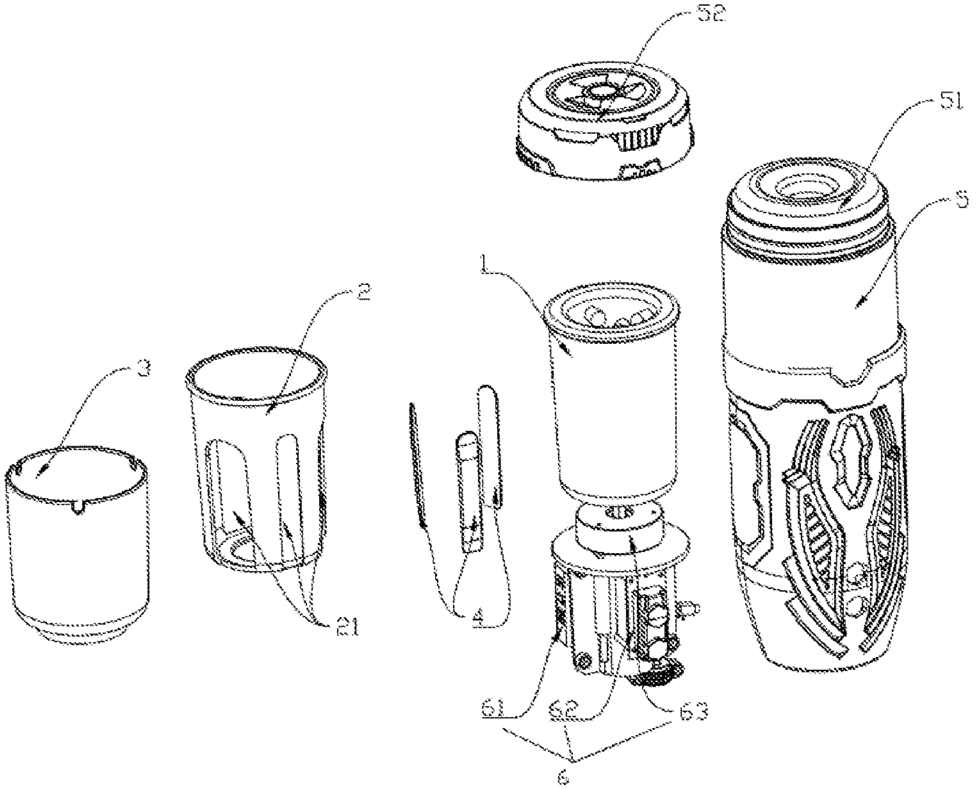
FIG. 4 is an explosive view of a sperm extractor of the utility model.

A sperm extractor is further provided. Refer to FIGS. 3-4, the sperm extractor comprises the multi-layer nested inner container as described above, and further comprises an outer housing 5 and a control component 6, wherein the inner container is fixed in an inner cavity of the outer housing 5 in a snap fit manner, an opening of the outer housing 5 is in the same direction as an opening of the inner container, the inner cavity of the outer housing also contains the control component 6, and a vibration part of the control component 6 is connected with the soft cup to control the vibration of the soft cup. In this way, the structure of the inner container is better protected, and more functions are realized.

In this embodiment, the opening of the outer housing 5 is further provided with a guide ring 51 in a snap fit manner, and a protective cover 52 is arranged on the guide ring. The guide ring and the protective cover together form a closed protective structure, which protects the inner environment of the inner container.

In this embodiment, the control component 6 comprises a battery 61, a circuit board 62 and a vibration motor 63 which are electrically connected, the circuit board 62 and the battery 61 are fixed to the outer housing, and an output end of the vibration motor 63 is connected with a bottom of the soft cup. A button and a charging port of the circuit board are exposed from the outer housing.

The utility model has the following advantages.

The soft cup can be well fixed by means of the hard inner long cylinder, and the soft material of the soft cup makes the interference fit structure easy to assemble and stable; the hard inner long cylinder is sleeved with the outer cylinder with a gap between the two; and at least part of an outer surface of the hard inner long cylinder is provided with stoppers, and the stoppers abut against the outer cylinder to form interference fit. Through the stoppers, snap fit is realized, so when the soft cup is pulled out, the hard inner long cylinder can be used as an acting point, which facilitates assembly and cleaning. In addition, the snap fit assembly mode is simple, so assembly efficiency is improved. Further, in the optimized scheme, the hard inner long cylinder is provided with through holes, and a user can reach to and hold the soft cup through the through holes for assembly, so that the assembly process is simple and the structure is more stable.

Only a few specific embodiments of the utility model are disclosed above, and the utility model is not limited thereto. Any changes that can be thought of by those skilled in the art shall fall within the scope of protection of the utility model.

What is claimed is:

1. A multi-layer nested inner container easy to disassemble and clean, comprising a soft cup, a hard inner long cylinder and an outer cylinder, wherein the soft cup is arranged in a cavity of the hard inner long cylinder in an interference fit manner to form a detachable assembly, the hard inner long cylinder is sleeved with the outer cylinder with a gap between the two, at least part of an outer surface of the hard inner long cylinder is provided with stoppers, and the stoppers abut against the outer cylinder to form interference fit;

wherein a side wall of the hard inner long cylinder is further provided with a plurality of through holes at intervals, and the stoppers are embedded in the side wall between adjacent through holes;

wherein the stoppers are silicone strips, and the silicone strip partially protrudes from a surface of the hard inner long cylinder.

2. The multi-layer nested inner container according to claim 1, wherein a surface of the stopper facing the outer cylinder is a friction surface.

3. The multi-layer nested inner container according to claim 1, wherein the hard inner long cylinder and the outer cylinder are made of hard plastic.

4. A sperm extractor, comprising a multi-layer nested inner container, an outer housing, and a control component;

wherein the multi-layer nested inner container comprises a soft cup, a hard inner long cylinder and an outer cylinder;

wherein the soft cup is arranged in a cavity of the hard inner long cylinder in an interference fit manner to form a detachable assembly, the hard inner long cylinder is sleeved with the outer cylinder with a gap between the two, at least part of an outer surface of the hard inner long cylinder is provided with stoppers, and the stoppers abut against the outer cylinder to form interference fit;

wherein the inner container is fixed in an inner cavity of the outer housing in a snap fit manner, an opening of the outer housing is in the same direction as an opening of the inner container, the inner cavity of the outer housing also contains the control component, and a vibration part of the control component is connected with the soft cup to control the vibration of the soft cup;

wherein the opening of the outer housing is further provided with a guide ring in a snap fit manner, and a protective cover is arranged on the guide ring.

5. The sperm extractor according to claim 4, wherein the control component comprises a battery, a circuit board and a vibration motor which are electrically connected, the circuit board and the battery are fixed to the outer housing, and an output end of the vibration motor is connected with a bottom of the soft cup.

6. A multi-layer nested inner container easy to disassemble and clean, comprising a soft cup, a hard inner long cylinder and an outer cylinder, wherein the soft cup is arranged in a cavity of the hard inner long cylinder in an interference fit manner to form a detachable assembly, the hard inner long cylinder is sleeved with the outer cylinder with a gap between the two, at least part of an outer surface of the hard inner long cylinder is provided with stoppers, and the stoppers abut against the outer cylinder to form interference fit;

wherein a side wall of the hard inner long cylinder is further provided with a plurality of through holes at intervals, and the stoppers are embedded in the side wall between adjacent through holes;

wherein a surface of the stopper facing the outer cylinder is a friction surface.

* * * * *